US011651860B2

(12) United States Patent
Kazemi Oskooei et al.

(10) Patent No.: US 11,651,860 B2
(45) Date of Patent: May 16, 2023

(54) DRUG EFFICACY PREDICTION FOR TREATMENT OF GENETIC DISEASE

(71) Applicant: International Business Machines Corporation, Armonk, NY (US)

(72) Inventors: Seyed Ali Kazemi Oskooei, Zurich (CH); Matteo Manica, Zurich (CH); Maria Rodriguez Martinez, Thalwil (CH); Jannis Born, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 986 days.

(21) Appl. No.: 16/413,399

(22) Filed: May 15, 2019

(65) Prior Publication Data

US 2020/0365270 A1 Nov. 19, 2020

(51) Int. Cl.
*G16H 50/20* (2018.01)
*G16B 20/00* (2019.01)
*G16B 5/20* (2019.01)
*G06N 3/08* (2023.01)

(52) U.S. Cl.
CPC .............. *G16H 50/20* (2018.01); *G06N 3/08* (2013.01); *G16B 5/20* (2019.02); *G16B 20/00* (2019.02)

(58) Field of Classification Search
CPC .......... G16H 50/20; G16B 5/20; G16B 20/00; G06N 3/08
See application file for complete search history.

(56) References Cited

U.S. PATENT DOCUMENTS

2014/0057798 A1 2/2014 Gong et al.
2017/0193157 A1 7/2017 Quirk et al.

FOREIGN PATENT DOCUMENTS

CN 107609326 A 1/2018
WO WO2019018780 A1 1/2019

OTHER PUBLICATIONS

Bahdanau et al., Neural machine translation by jointly learning to align and translate, arXiv preprint arXiv:1409.0473, 2014, 15 pages.
Vaswani et al., Attention is all you need, Advances in neural information processing systems, 2017, pp. 5998-6008.
Yang et al., Hierarchical attention networks for document classification, Proceedings of the 2016 conference of the North American chapter of the association for computational linguistics: human language technologies, Jun. 2016, pp. 1480-1489.
Schwaller, et al., Found in Translation: predicting outcomes of complex organic chemistry reactions using neural sequence-to-sequence models, Chemical science, 9(28), 2018, pp. 6091-6098. DOI: 10.1039/C8SC02339E.
Lloyd, et al., Pharma r&d annual review 2017, Available at: pharmaintelligence.informa.com/resources/product-content/pharma-rd-annual-review-2018, Accessed Jun. 25, 2018, 2017, 44 pages.
Hargrave-Thomas, et al., Serendipity in anticancer drug discovery, World journal of clinical oncology 3.1, 2012, 17 pages doi: 10.5306/wjco.v3.i1.1.
Garnett, et al., Systematic identification of genomic markers of drug sensitivity in cancer cells, Nature 483 No. 7391, 2012, pp. 570-575 (Abstract Only).
Yang et al., Genomics of Drug Sensitivity in Cancer (GDSC): a resource for therapeutic biomarker discovery in cancel cells, Nucleic acids research 41.D1, 2012, pp. D955-D961.
Barretina et al., The Cancer Cell Line Encyclopedia enables predictive modeling of anticancer drug sensitivity, Nature 483, No. 7391, 2012, pp. 603-607 (Author Manuscript).
Cancer Genome Atlas Network. "Comprehensive molecular portraits of human breast tumours." Nature 490, No. 7418 (2012): 61-70.
Heiser, et al., Subtype and pathway specific responses to anticancer compounds in breast cancer, Proceedings of the National Academy of Sciences, 2012, 109(8), pp. 2724-2729.
International Cancer Genome Consortium, International network of cancer genome projects, Nature 464, 7291, 2010, pp. 993-996.
Lamb, et al., The Connectivity Map: using gene-expression signatures to connect small molecules, genes, and disease, Science, 313(5795), 2006, pp. 1929-1935.
Shoemaker, The NCI60 human tumor cell line anticancer drug screen, Nature Reviews Cancer 6, No. 10, 2006, pp. 813-823.
Costello, et al., A community effort to assess and improve drug sensitivity prediction algorithms, Nature biotechnology 32, No. 12, 2014, pp. 1202-1214.
Geeleher, Cancer biomarker discovery is improved by accounting for variability in general levels of drug sensitivity in pre-clinical models, Genome biology 17, No. 1, 2016, 190, 11 pages.
Menden et al., Machine learning prediction of cancer cell sensitivity to drugs based on genomic and chemical properties, PLoS one vol. 8, No. 4, 2013, e61318, 10 pages.
Karelson, et al., Quantum-chemical descriptors in QSAR/QSPR studies, Chem. Rev., vol. 96, No. 3, pp. 1027-1044, 1996.

(Continued)

*Primary Examiner* — Jerry Lin
(74) *Attorney, Agent, or Firm* — Daniel Morris; Otterstedt & Kammer PLLC

(57) ABSTRACT

A neural network model is generated for drug efficacy prediction in treatment of genetic disease from a dataset correlating biomolecular data for disease-cell samples with drug efficacy values for a plurality of drugs, including defining training data pairs each including biomolecular data for a sample represented in the dataset and a string representation of a drug represented in the dataset; and using the training data pairs and the drug efficacy values corresponding to respective pairs to train weights of the model including a first attention-based encoder which encodes the biomolecular data of each pair, to produce encoded biomolecular data, a second attention-based encoder which encodes the string representation of each pair, to produce encoded string data, and a set of neural network layers which process the encoded biomolecular and string data for each pair, to produce a model output corresponding to drug efficacy.

11 Claims, 5 Drawing Sheets

(56) References Cited

OTHER PUBLICATIONS

Cereto-Massague, et al., Molecular fingerprint similarity search in virtual screening, Methods 71, 2015, pp. 58-63.
Luong et al., Effective approaches to attention-based neural machine translation, arXiv preprint arXiv:1508.04025, 2015, 11 pages.
Wu et al., Google's neural machine translation system: Bridging the gap between human and machine translation, arXiv preprint arXiv:1609.08144, 2016, 23 pages.
Chen et al., The rise of deep learning in drug discovery, Drug Discovery Today, vol. 23, No. 6, pp. 1241-1250, Jun. 2018.
Chang et al., Cancer Drug Response profile scan (CDRscan): a deep learning model that predicts drug effectiveness from cancer genomic signature, Scientific reports 8, No. 1, 2018, 11 pages.
Oskooei et al., PaccMann: Prediction of anticancer compound sensitivity with multi-modal attention-based neural networks, arXiv preprint arXiv:1811.06802, 2018, 13 pages.
Matteo Manica et al., Protein-Targeted Drug Compound Identification Unpublished U.S. Appl. No. 17/004,104, filed Aug. 27, 2020, pp. 1-25 plus 5 sheets drawings.
Paul J. Otterstedt, List of IBM Patents or Patent Applications Treated as Related, Nov. 27, 2020, pp. 1-2.
Manica et al., Towards Explainable Anticancer Compound Sensitivity Prediction via Multimodal Attention-based Convolutional Encoders, ICML2019, Jun. 14, 2019, Grace Period Disclosure 11 Pages.
Manica et al., Deep learning for disease-driven drug design, https://www.meetup.com/Deep-Learning-Zurich-DLZH/events/261927228/, Jun. 25, 2019. Grace Period Disclosure 51 Pages.
Merolla et al., A Million Spiking-Neuron Integrated Circuit with a Scalable Communication Network and Interface, Science, vol. 345, Issue 6197, 2014, 7 pages.

Yang et al., Hierarchical Attention Networks for Document Classification, Proceedings of the 2016 Conference of the North American Chapter of the Association for Computational Linguistics: Human Language Technologies, pp. 1480 to 1489, 2016.
Williams, Simple Statistical Gradient-Following Algorithms for Connectionist Reinforcement Learning, Mach. Learn. 8, 229-256 (1992).
Le Tourneau et al., Treatment Algorithms Based on Tumor Molecular Profiling: The Essence of Precision Medicine Trials, JNCI Journal of the National Cancer Institute, 2016, 108(4): djv362, 10 pages.
Olivecrona et al., Molecular De-Novo Design through Deep Reinforcement Learning, Cornell University Library, Computer Science, Artificial Intelligent, arXiv:1704.07555, Apr. 25, 2017.
Seyed Ali Kazemi Oskooei et al., unpublished U.S. Appl. No. 16/685,455, filed Nov. 15, 2019, Drug Compound Identification for Target Tissue Cells, pp. 1-24 plus 5 sheets of drawings.
Paul J. Otterstedt, List of IBM Patents or Patent Applications Treated as Related, Dec. 19, 2019, pp. 1-2.
Petrova, "Innovation in the pharmaceutical industry: The process of drug discovery and development," in Innovation and marketing in the pharmaceutical industry, Springer, 2014, pp. 19-81.
Goh, et al., "SMILES2Vec: An Interpretable General-Purpose Deep Neural Network for Predicting Chemical Properties," ArXiv Prepr. ArXiv171202034, 2017, 8 Pages.
Chang Y, Park H, Yang HJ, Lee S, Lee KY, Kim TS, Jung J, Shin JM. Cancer Drug Response profile scan (CDRscan): a deep learning model that predicts drug effectiveness from cancer genomic signature. Scientific reports. Jun. 11, 2018;8(1):8857.
"PaccMann: Prediction of anticancer compound sensitivity with multi-modal attention-based neural networks", Oskooei et al. arXiv:1811.06802v1 [cs.LG], Nov. 16, 2018. Grace Period Disclosure pp. 1-13.

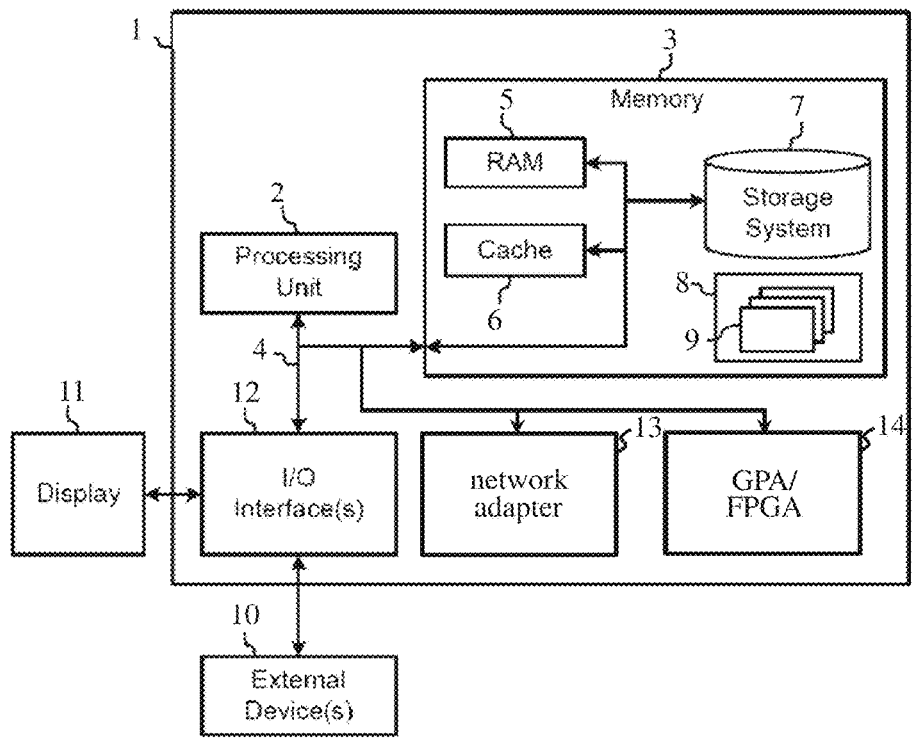
Figure 1
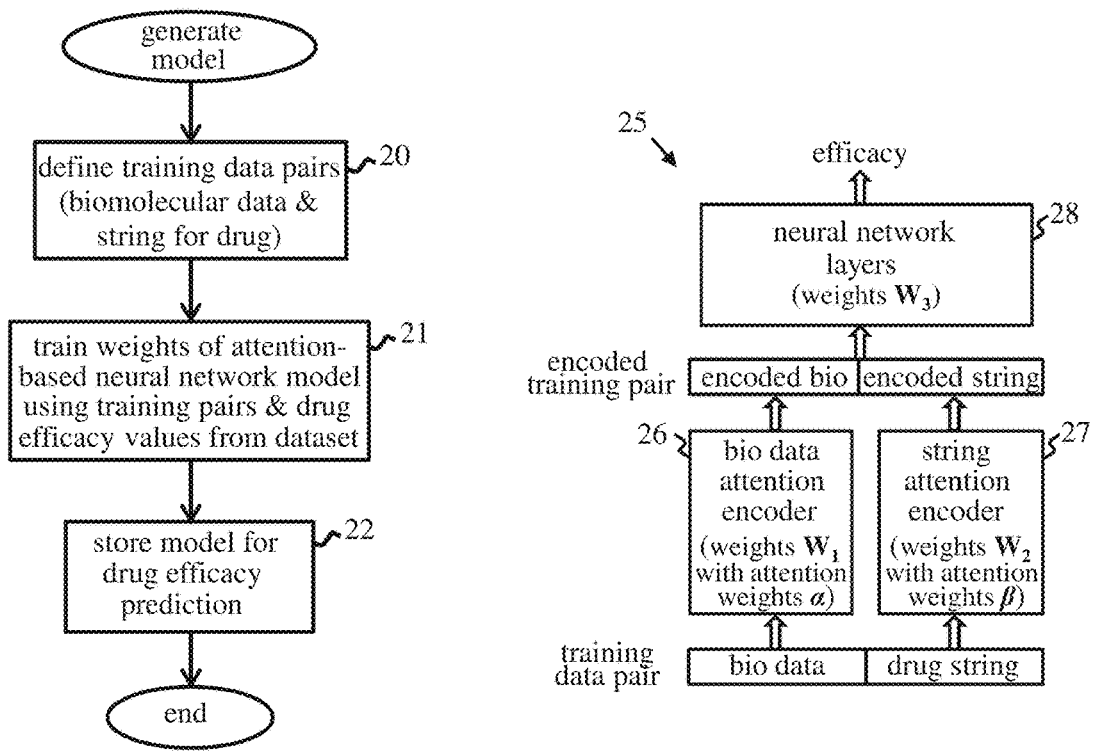
Figure 2
Figure 3

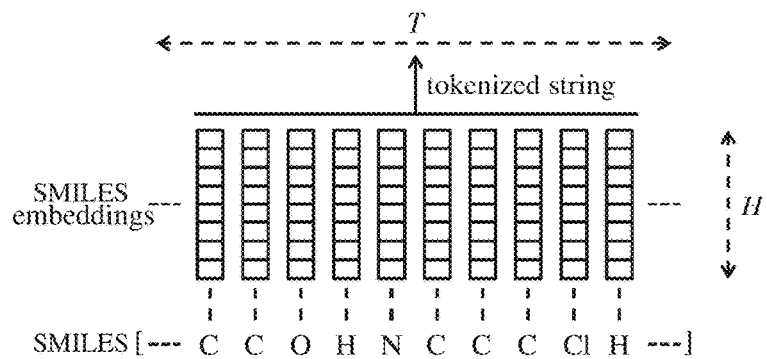
Figure 9
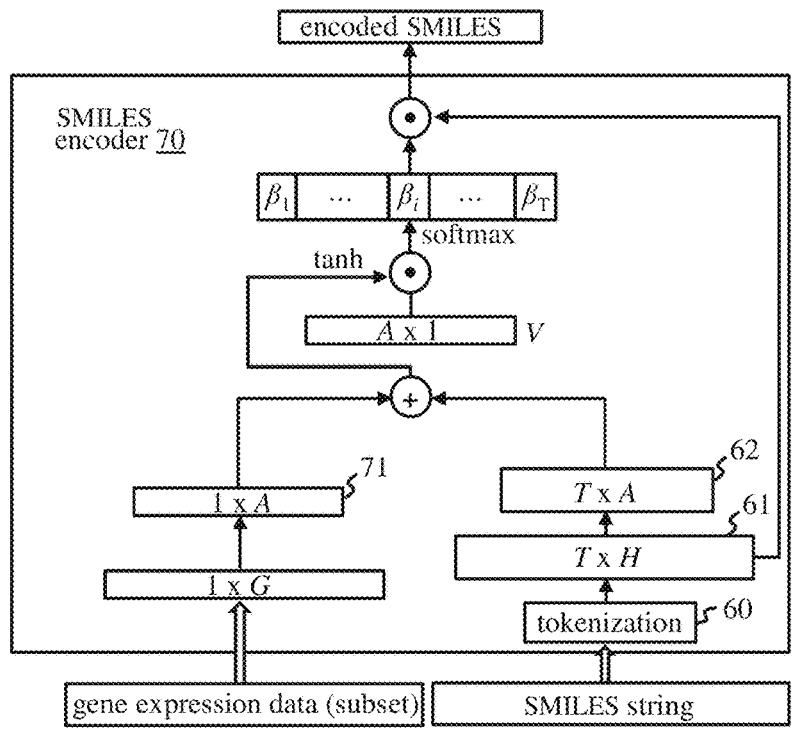
Figure 10
| Model | Drug structure | Best RMSE | Average RMSE |
|---|---|---|---|
| Baseline | fingerprints | 0.114 | 0.123 ± 0.008 |
| Fig. 8 (SA) | SMILES | 0.089 | 0.112 ± 0.007 |
| Figs. 8 & 10 (CA) | SMILES | 0.095 | 0.110 ± 0.008 |
Figure 11

| Drug | Cell line | Cancer type | Top-5 attended genes | IC50 Predicted | IC50 Measured |
|---|---|---|---|---|---|
| Afatinib | UMC-11 | lung (NSCLC) | F13A1, MYH4, ATOH8, SEMA4A, NES | 0.505 | 0.493 |
| BX-912 | YH-13 | glioma | RNASE2, HOXA13, CBR3, FABP1, HDC | 0.532 | 0.5 |
| GSK319347A | EW-12 | bone | CD300A, RHBDL2, NES, TFF3, SOCS1 | 0.597 | 0.7 |
| JW-7-24-1 | OVTOKO | ovary | HDC, EIF2A, RNASE2, ANGPTL6, CBR3 | 0.502 | 0.49 |
| PI-103 | MV-4-11 | leukemia | TFF3, ATOH8, RBP2, ITIH3, GRIP1 | 0.362 | 0.33 |
| TGX221 | SW962 | urogenital system | CBR3, RNASE2, FABP1, HDC, SH3D21 | 0.621 | 0.66 |
| S-Trityl-L-cysteine | NCI-H187 | lung (SCLC) | RHBDL2, NR1H4, MYH4, NES, APCS | 0.535 | 0.502 |
| Fedratinib | BL-41 | lymphoma | TFF3, ATOH8, RBP2, MAPK7, ARHGEF33 | 0.382 | 0.428 |
| Tipifarnib | RCC10RGB | kidney | EIF2A, HDC, CBR3, PIK3R5, HOXA13 | 0.542 | 0.544 |
| Midostaurin | GAK | skin | SVOP, FABP1, HDC, F13A1, FGFR3 | 0.507 | 0.477 |

Figure 12

DRUG EFFICACY PREDICTION FOR TREATMENT OF GENETIC DISEASE

STATEMENT REGARDING PRIOR DISCLOSURES BY THE INVENTOR OR A JOINT INVENTOR

The following disclosure is submitted under 35 U.S.C. 102(b)(1)(A): "PaccMann: Prediction of anticancer compound sensitivity with multi-modal attention-based neural networks", Ali Oskooei, Jannis Born, Matteo Manica, Vigneshwari Subramanian, Julio Sáez-Rodriguez, and Maria Rodriguez Martinez, arXiv:1811.06802v1 [cs.LG], 16 Nov. 2018.

BACKGROUND

The present invention relates generally to drug efficacy prediction for treatment of genetic disease, and more particularly to generation and use of neural network models for drug efficacy prediction in such treatment.

Typically, a genetic disease is not one disease but rather a collection of related diseases. Different patients suffering from a single type of cancer, for example, may have different genetic mutations and, potentially, need a different course of treatment. There is strong evidence that tumor's genetic makeup can influence the outcome of anti-cancer drug treatment resulting in heterogeneity in clinical response of various subjects to a certain drug. This has led to the promise of personalized (or precision) medicine where biomolecular data, such as gene expression data or other molecular biomarkers obtained from a patient, may be used to design a personalized course of treatment.

Large datasets have emerged linking genomic profiles to efficacy of pharmaceutical drugs. Such datasets correlate biomolecular data of different disease-cell samples with measured drug efficacy values, e.g. half maximal inhibitory concentration ($IC_{50}$) values, and thus indicate sensitivity of disease cells with various genetic characteristics to particular pharmaceutical drugs. Machine learning can be used to harness this data in the interests of precision medicine. Machine learning provides techniques for processing (often massive) datasets from a real-word application in relation to a basic model for the application in order to train, or optimize, the model for the application in question. The model can then be applied to perform inference tasks based on new (unseen) data generated in that application.

Machine learning models based on artificial neural networks perform computational tasks in a manner inspired by biological architectures of the nervous system. These networks are based on a fundamental principle of biological systems whereby neurons are interconnected via synapses which relay weighted signals between the neurons. Neural network models are based on a logical construction in which a succession of layers of neurons are interconnected so that output signals of neurons in one layer are weighted and transmitted to neurons in the next layer. Each neuron in a given layer can be connected to one or more neurons in the next layer, and different weights can be associated with respective neuron-neuron connections. Each neuron generates output signals dependent on its accumulated inputs, whereby weighted signals can be propagated over successive layers of the network.

The sets of weights associated with the various layers of a neural network model are learned during the model training operation. The weights are trained via an iterative process in which the network is exposed to a set of training data and the weights are repeatedly updated as the network "learns" from the training data. Training involves an iterative cycle of signal propagation and weight-update calculation operations, with the network weights being progressively updated until a convergence condition is achieved. The resulting trained network model, with the trained weights defined via this process, can then be applied for inference.

SUMMARY

According to at least one embodiment of the present invention there is provided a computer-implemented method for generating a neural network model for drug efficacy prediction in treatment of genetic disease from a dataset correlating biomolecular data for disease-cell samples with drug efficacy values for a plurality of drugs. The method includes defining training data pairs each comprising biomolecular data for a sample represented in the dataset and a string representation of a drug represented in the dataset. The method further comprises using the training data pairs and the drug efficacy values corresponding to respective pairs to train weights of a neural network model comprising a first attention-based encoder which encodes the biomolecular data of each pair, using a first set of the weights, to produce encoded biomolecular data, a second attention-based encoder which encodes the string representation of each pair, using a second set of the weights, to produce encoded string data, and a set of neural network layers which process the encoded biomolecular and string data for each pair, using a third set of the weights, to produce a model output corresponding to drug efficacy. The trained model is then stored for drug efficacy prediction.

At least one additional embodiment of the invention provides a computer program product comprising a computer readable storage medium embodying program instructions, executable by a computing system, to cause the computing system to perform a method for generating a neural network model for drug efficacy prediction as described above.

At least one further embodiment of the invention provides a computer-implemented drug efficacy prediction method. The method includes defining an inference data pair comprising biomolecular data for a disease-cell sample and a string representation of a drug to be tested for efficacy in relation to that sample. The method further comprises supplying the inference data pair to a neural network model generated by a method as described above to obtain a model output predictive of efficacy of the drug.

Embodiments of the invention will be described in more detail below, by way of illustrative and non-limiting example, with reference to the accompanying drawings.

BRIEF DESCRIPTION OF THE DRAWINGS

FIG. 1 is a schematic representation of a computer for implementing neural network model generation and drug efficacy prediction methods embodying the invention;

FIG. 2 indicates steps of a neural network model generation method embodying the invention;

FIG. 3 is a schematic representation of a neural network model architecture for the FIG. 2 method;

FIG. 9 illustrates a tokenization step performed in the FIG. 8 architecture;

FIG. 10 is a schematic representation of an alternative attention-based encoder for the FIG. 8 architecture;

FIG. 11 characterizes results obtained with the embodiments of FIGS. 8 and 10; and FIG. 12 indicates drug efficacy prediction results for the FIG. 8 embodiment.

DETAILED DESCRIPTION

Figure 4:
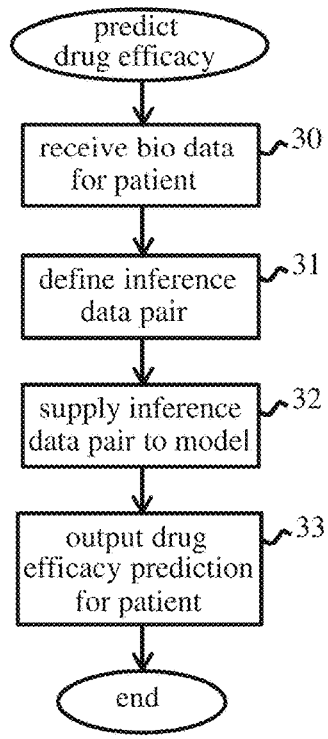
FIG. 4 indicates steps of a drug efficacy prediction method embodying the invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments to be described may be performed as computer-implemented methods for generating neural network models for drug efficacy prediction in treatment of genetic disease. The methods may be implemented by a computing system comprising one or more general- or special-purpose computers, each of which may comprise one or more (real or virtual) machines, providing functionality for implementing the operations described herein. Steps of methods embodying the invention may be implemented by program instructions, e.g. program modules, implemented by a processing apparatus of the system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

FIG. 1 is a block diagram of exemplary computing apparatus for implementing methods embodying the invention. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

Memory 3 may include at least one program product having one or more program modules that are configured to carry out functions of embodiments of the invention. By way of example, program/utility 8, having a set (at least one) of program modules 9, may be stored in memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g., network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g., the Internet) via network adapter 13. As depicted, network adapter 13 communicates with the other components of computer 1 via bus 4. Computer 1 may also communicate with additional processing apparatus 14, such as a GPU (graphics processing unit) or FPGA, for implementing embodiments of the invention. It should be understood that although not shown, other hardware and/or software components could be used in conjunction with computer 1. Examples include, but are not limited to: microcode, device drivers, redundant processing units, external disk drive arrays, RAID systems, tape drives, and data archival storage systems, etc.

In embodiments below, neural network models for drug efficacy prediction are generated by processing training data derived from a dataset which correlates measured biomolecular data for disease-cell samples with measured drug efficacy values for a plurality of drugs tested in relation to samples in the dataset. Such datasets may include various types of biomolecular data for disease cells, e.g. gene expression data, protein levels, genomic data, copy number alteration and/or other molecular biomarkers, which provide a biomolecular profile of a disease cell. Drug efficacy values may be expressed, for example, as $IC_{50}$ values. While $IC_{50}$ values are widely used as a measure of drug efficacy, in general any measurement values indicating sensitivity of genetic processes to a drug may be used as drug efficacy values.

FIG. 2 indicates basic steps of a model generation method embodying the invention. The method can be implemented by a computing system 1 using a dataset which may be stored locally, in memory 3 of the computing system, or stored remotely and accessed by system 1 via a network. In step 20, computing system 1 defines a set of training data pairs based on data in the dataset. Each training data pair comprises biomolecular data for a cell sample in the dataset, and a string representation of a drug for which a drug efficacy value is specified in the dataset in relation to that sample. In general, the biomolecular data used in training data pairs may comprise data items corresponding to one or more types of biomolecular data, e.g. gene expression values, protein levels, etc., for samples in the training dataset. Depending on content of the dataset, the training data pairs may be generated automatically in computing system 1 by analysis of the dataset in step 20. In some embodiments, all data required to define the training data pairs may be contained in the dataset. In other embodiments, data from the dataset may be supplemented with data from other sources, e.g. via operator input, to define the training data pairs. As a particular example, string representations for drugs represented in the dataset may be defined via operator input in step 20. String representations, such as SMILES (simplified molecular-input line-entry system) strings and SMARTS (SMILES arbitrary target specification) strings, are well-known line notations for representing the chemical structure of a molecule in a raw form. These raw data strings are distinct from other representations, such as fingerprints or chemical descriptors, which are based on engineered features that describe the chemical properties and structure of a compound.

In step 21 of FIG. 2, computing system 1 uses the training data pairs, and the drug efficacy values corresponding to respective pairs, to train weights of a neural network model. The basic architecture of this model is shown in FIG. 3. The model 25 includes a first attention-based encoder, indicated as bio data attention encoder 26, which encodes the biomolecular ("bio") data of each training pair using a first set ($W_1$) of the neural network weights. This set of weights $W_1$ includes attention weights, denoted by a, for the attention encoder 26. Model 25 also includes a second attention-based encoder, indicated as string attention encoder 27, which encodes the string representation of each training pair using a second set ($W_2$) of the neural network weights. This set of weights $W_2$ includes attention weights, denoted by β, for the attention encoder 27. The encoded biomolecular data produced by bio attention encoder 26, and the encoded string data produced by string attention encoder 27, define an encoded training pair which is supplied to a set of neural network layers 28. These network layers 28 process the encoded biomolecular and string data of each encoded training pair, using a third set ($W_3$) of the neural network weights, to produce a model output corresponding to drug efficacy.

The training process of step 21 is performed in generally known manner via an iterative cycle of signal propagation and weight-update calculation operations in response to the training data pairs which are successively supplied as inputs to the network. Briefly, for each training pair, the signal propagation operation comprises a forward propagation operation in which the training data is forward-propagated over the network, and a backpropagation operation in which error signals are back-propagated over the network. In the forward propagation operation, the input data signals are propagated through the network layers and weighted by the network weights $W_1$, $W_2$ and $W_3$ in the attention encoders 26, 27 and the final stage of layers 28. For an output neuron of stage 28, the output signal after forward propagation is compared with the expected output for the current training pair to obtain an error signal E. (The known drug efficacy values corresponding to respective training pairs provide the labels for the supervised learning process, whereby the expected output here is determined by the drug efficacy value for the current training pair). The error signal is then backpropagated through the network layers, and the back-propagated error signals are weighted by the appropriate network weights as before. Backpropagation thus results in computation of error signals for the different layers of the network. Updates to the weights associated with particular network layers can be calculated, based on the signals propagated by the neuron layers in the signal propagation operations, to correct the weights and move towards an optimal weight set. These weight-updates can be calculated in various ways, depending on network implementation details, as is well-known in the art. The training process thus progressively updates the network weights until a convergence condition is achieved. Convergence can be defined in various known ways, e.g. as the point at which the error (also known as loss) cannot be reduced any further, and the particular convergence condition is orthogonal to the operation described herein.

During forward propagation, the input bio data and string data of a training pair is encoded by attention encoders 26 and 27 respectively using the weights $W_1$ and $W_2$ which include the attention weights α and β. Attention-based encoders are well-known in the machine learning field and have been successfully applied in various tasks such as machine translation, document classification, and predicting products of chemical reactions (see, for example: "Neural Machine Translation by Jointly Learning to Align and Translate", Bandanau et al., arXiv preprint arXiv:1409.0473 (2014); "Attention is All You Need", Ashish Vaswani et al., Advances in Neural Information Processing Systems, pp. 5998 to 6008, 2017; "Hierarchical Attention Networks for Document Classification", Zichao Yang et al., Proceedings of the 2016 Conference of the North American Chapter of the Association for Computational Linguistics: Human Language Technologies, pp. 1480 to 489, 2016; and "Found in Translation: Predicting Outcomes of Complex Organic Chemistry Reactions using Neural Sequence-to-Sequence Models", Philippe Schwaller et al., Chemical science 9(28), pp. 6091 to 6098, 2018). Briefly, attention-based encoders are implemented by a neural network structure which projects the input into an attention space and distributes attention over different parts of the input, according to different weights which determine the degree of importance attached to the various parts of the input. The attention weights are learned and used to comparatively weigh different features of the inputs in encoders 26 and 27 according to their relative contribution in making a better overall prediction (i.e. lowering the error or loss). The inputs to encoders 26 and 27 are then masked using these learned attention weights and the masked feature sets are paired and fed to layers 28. The attention weights α and β in encoders 26 and 27 are learned during the iterative training process in which the weights are iteratively updated as described above. Bio attention encoder 26 thus learns the attention weights α which distribute attention over content of the bio data in the input training pair. Similarly, string attention encoder 27 learns the attention weights β which distribute attention over content of the string data in the input training pair. Exemplary implementations for the attention encoders 26 and 27 are described in more detail below.

On completion of the training process in step 21 of FIG. 2, the resulting trained network model, with the trained weights $W_1$, $W_2$ and $W_3$, is stored in step 22. The trained model can then be applied in inference operations for drug efficacy prediction. Since the model is generated based on biological data for disease cells and the raw string representation of drugs, the trained model effectively characterizes the link between the molecular structure of drug compounds, biomarkers of disease cells and drug response. The use of attention-based encoders enables the model to learn the most informative features from the raw input data, and also renders the resulting model explainable and interpretable. Methods embodying the invention offer highly-accurate drug-efficacy prediction models which can be used to test efficacy of any drug for a disease based on a string representation of that drug, regardless of the particular set of drugs used to train the model.

A model generated by the FIG. 2 method can be used to predict drug efficacy by defining an inference data pair comprising biomolecular data for a disease-cell sample and a string representation of the drug to be tested for efficacy in relation to that sample. The inference data pair can then be supplied to the model, in equivalent manner to a training data pair, to obtain a model output predictive of efficacy of the drug. FIG. 4 indicates steps involved in predicting efficacy of a drug for a particular patient's disease. After storing a model generated as described above, the biomolecular data measured for a patient is input to computing system 1. This biomolecular data is obtained in known manner by analysing a disease-cell sample obtained from the patient. For a patient suspected to suffer from a certain type of cancer, for example, tumor biopsy is generally performed to obtain the biomolecular data. The patient's biomolecular data is received by system 1 in step 30 of FIG. 4. In step 31, the system defines an inference data pair comprising the biomolecular data of the patient and a string representation of a drug to be tested for efficacy in treatment of that patient. The form of the inference data pair corresponds to that of the training data pairs, whereby the bio data of the inference pair comprises the patient's bio data for the bio data items in the training pairs. In step 32, the system supplies the resulting inference data pair to the trained model to obtain a model output predictive of efficacy of the drug for that patient. The model output here may comprise a predicted drug efficacy value, e.g. an $IC_{50}$ value. However, depending on how the labels are defined for the supervised training based on drug efficacy values, the model output may otherwise indicate drug efficacy, e.g. as a predicated range of $IC_{50}$ values or some other efficacy rating or classification. In step 33, the drug efficacy prediction is output by system 1 for use in treatment planning for the patient.

Figure 5:
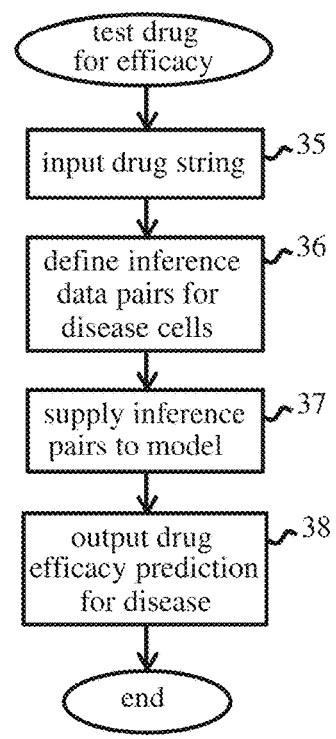
FIG. 5 indicates steps of another drug efficacy prediction method embodying the invention.

The FIG. 4 method can be used to examine potential efficacy of multiple drugs. This allows efficacy comparisons and formulation of treatment plans personalized to individual patients. Models generated by methods embodying the invention can also be applied to test a new or potentially-useful drug for efficacy against a particular disease. FIG. 5 indicate steps of such a drug efficacy prediction method. In step 35, a string representation of the drug to be tested is input to system 1. In step 36, the system defines a plurality of inference data pairs. These inference pairs comprise biomolecular data for respective disease-cell samples, e.g. from the training dataset used to generate the model, and the drug string input in step 35. In step 37, the system supplies the resulting inference data pairs successively to the trained model to obtain a plurality of model outputs corresponding to respective samples. This set of outputs are collectively predictive of efficacy of the drug in treatment of the disease in question. System 1 then outputs a drug efficacy prediction (e.g. as the set of model outputs per se, or a further processed analysis thereof) in step 38 for assessing usefulness of the drug in treating the disease.

Figure 6:
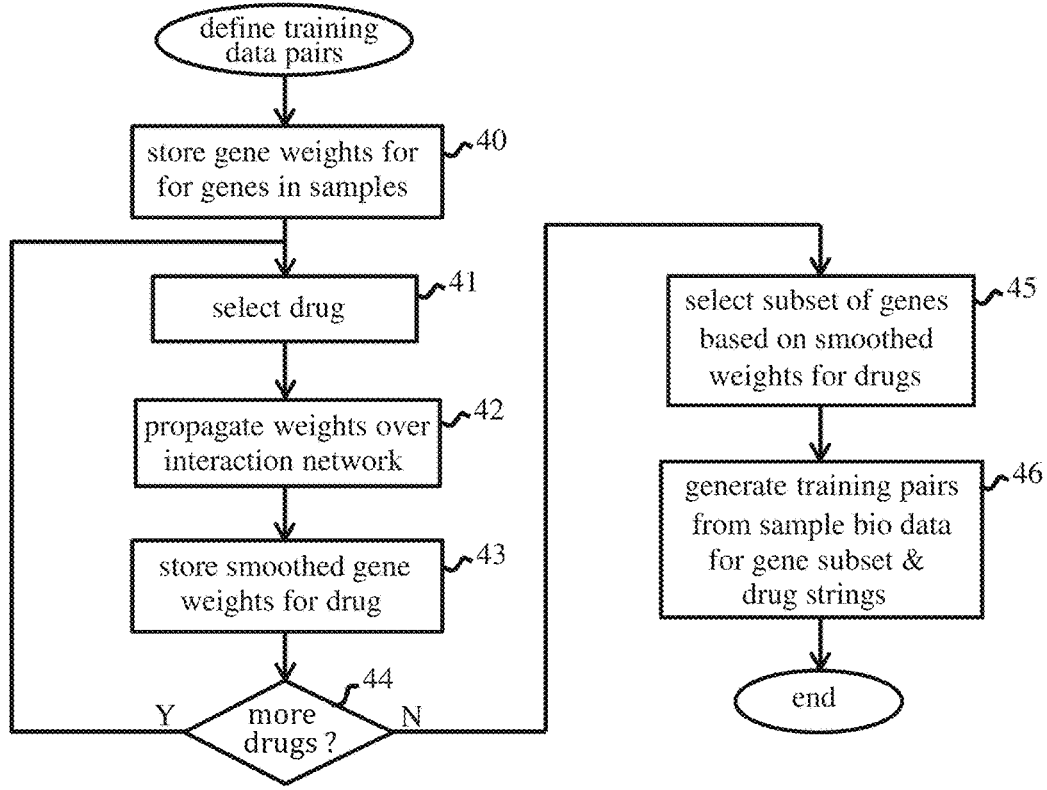
FIG. 6 indicates additional steps in a preferred embodiment of the model generation method.

In preferred methods embodying the invention, the training data pairs are defined after preprocessing biomolecular data for samples in the dataset to identify potentially-more-relevant data items. Steps of this operation are indicated in FIG. 6. The preprocessing operation uses a set of gene weights which is defined for each drug used in the training pairs. The gene weights for each drug correspond to respective genes in the cell-samples, and each gene weight is dependent on predetermined relevance of the respective gene to efficacy of the drug. Relevance of a gene to efficacy of a pharmaceutical drug is determined based on prior knowledge, e.g. obtained from published literature, experimental results, computational analysis, data mining, etc., indicating known or predicted sensitivity of genetic characteristics to action of a particular drug. For example, a gene (or more particularly a gene whose functional product) is a known drug target can be deemed highly relevant to efficacy of the drug. Similarly, genes having known/predicted interactions or effects on a drug target gene may be considered relevant to drug efficacy here. Gene weights are assigned to genes in the cell samples according to their relevance as determined from the prior knowledge sources, e.g. with relevant genes being assigned a higher bias weight than non-relevant genes. For example, each gene weight may be selected as one of two values, a higher value and a lower value, dependent on predetermined relevance and non-relevance respectively of the corresponding gene to drug efficacy. The gene weights thus defined based on prior knowledge for each drug are stored in memory 3 of system 1 in step 40 of FIG. 6.

In step 41 of FIG. 6, system 1 selects a particular drug for which gene weights are stored in the system. In step 42, the system retrieves the set of gene weights for the selected drug, and propagates these weights over a predetermined network, indicating interaction between genes in the cell samples, to obtain smoothed gene weights for respective genes. The network used here may be the STRING protein-protein interaction (PPI) network, or other similar network, which defines interactions between genes (or more particularly gene-products such as proteins), represented by nodes in a network over which values can be propagated and modified (smoothed) based on interactions between nodes as defined in the network. Such networks of molecular interactions can be obtained from a variety of sources, and may be pre-stored in system 1 or accessed remotely for the propagation step. The resulting set of smoothed weights for the drug is stored in system 1 in step 43.

In decision step 44, the system checks whether any further drugs remain to be selected. If so, ("Yes" (Y) at decision block 44), then operation reverts to step 41 and steps 41 to 43 are repeated for the next drug. When all drugs have been accommodated ("No" (N) at decision block 44), operation proceeds to step 45. Here, system 1 selects a subset of genes in the cell-samples in dependence on the smoothed gene weights for each drug. The objective here is to include in the subset those genes whose smoothed weights indicate particular relevance to drug efficacy. This can be done in various ways, e.g. by selecting any gene having a smoothed weight above a threshold level. In embodiments where the (unprocessed) gene weights comprise one of a higher value and a lower value (indicating relevance and non-relevance respectively) of the gene, the gene subset may be selected by selecting, for each drug, a plurality of genes having the highest smoothed gene weights for that drug. In step 46, the training data pairs are then generated such that the biomolecular data of a training pair comprises biomolecular data for the selected subset of genes in a cell-sample.

The preprocessing of FIG. 6 focusses the subsequent training operation on the most relevant bio data based on prior knowledge. The propagation of the gene weights integrates prior knowledge about molecular interactions, defining neighborhoods of influence around the drug targets, and simulates the spread of perturbations within the cell following drug administration. The operation also serves to reduce processing complexity and training time by reducing the amount of training data to be processed by the model.

This offers exceptionally efficient model generation methods and enhanced accuracy in the resulting models.

Figure 7:
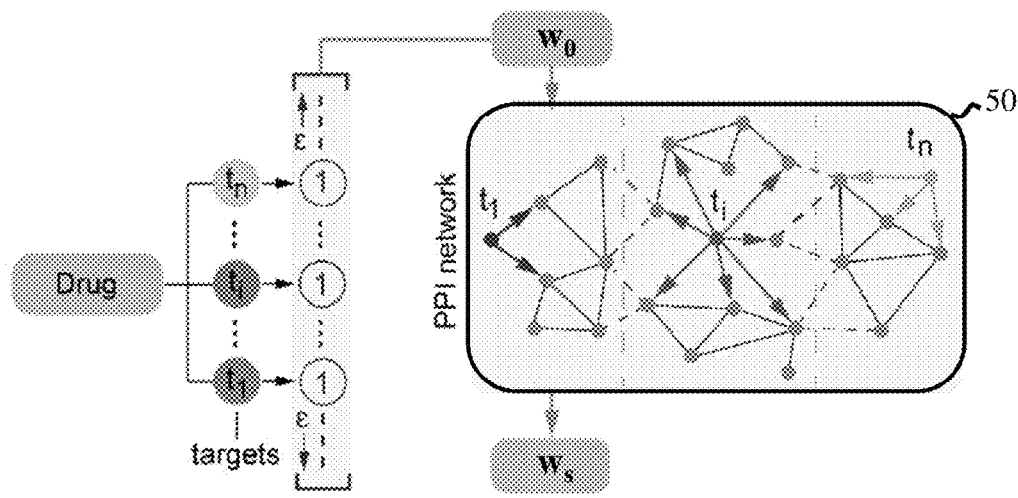
FIG. 7 illustrates features of an exemplary implementation of the FIG. 6 method.
Figure 8:
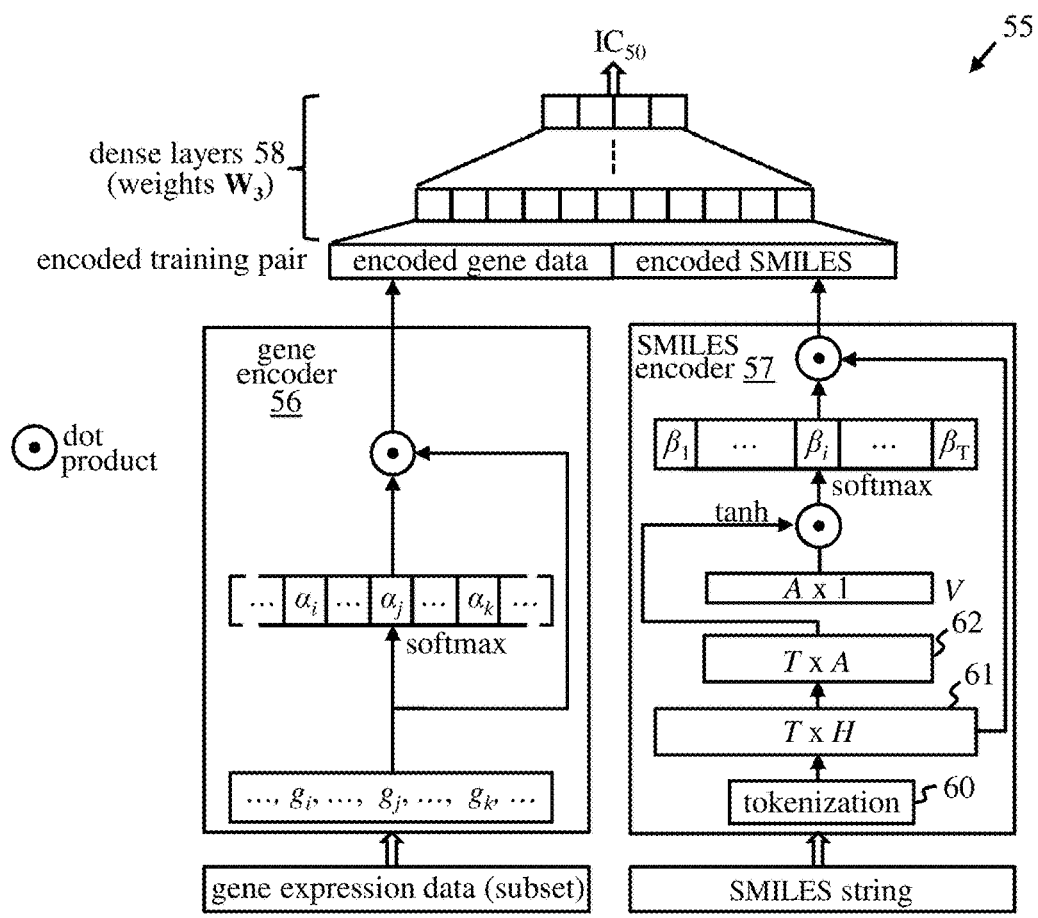
FIG. 8 shows a more detailed model architecture for an embodiment of the neural network model generation method.

A preferred implementation of the model generation method is illustrated in more detail in FIGS. 7 and 8. The method was applied to the gene expression and drug $IC_{50}$ data publicly available as part of the GDSC (Genomics of Drug Sensitivity in Cancer) dataset. The dataset includes the results of screening on more than a thousand genetically profiled human pan-cancer cell lines with a wide range of anticancer compounds. Within the GDSC database, 221 compounds were targeted therapies and, of these, the molecular structures of 208 compounds were publicly available. For these 208 compounds, canonical SMILES strings were collected, and Morgan fingerprints were also acquired for a baseline comparison model explained below. Exploiting the property that most molecules have multiple valid SMILES strings, we adopted a data augmentation strategy and represented each anticancer compound with 32 SMILES strings. This resulted in a dataset consisting of 6,556,160 drug-cell pairs.

Gene expression data was selected as the bio data for the training pairs as it has been shown to be more predictive of drug sensitivity than genomics (i.e., copy number variation and mutations) or epigenomics (i.e., methylation) data. The gene expression data comprises measurement values relating to individual genes, and in particular the functional products of these genes, in the cell samples. Typically, gene expression data comprises relative (with respect to a control sample) mRNA abundance measurements for mRNAs transcribing every gene within a cell sample. The initial weighting and propagation scheme of FIG. 6 was implemented to reduce the dimensionality of the cell lines' transcriptomic profile, consisting of 16,000 genes, to a smaller subset containing the most informative genes. The implementation is illustrated schematically in FIG. 7. For each drug, an initial gene weight of $W_0=1$ was given to the reported drug target genes, and a small positive weight of $W_0=\varepsilon=1e-5$ was assigned to all other genes. The resulting weights vector $w_0$ was smoothed by propagation over the STRING PPI network as indicated schematically at 50. The network smoothing of the weights can be described as a random walk propagating the initial weights $W_0$ throughout the network. We denote the string network as $S=(P, E, A)$ where P are the protein vertices of the network, E are the edges between the proteins and A is the weighted adjacency matrix indicating the level of confidence about the existence of a certain interaction. The smoothed weights were determined iteratively from the following function:

$$W_{t+1} = \alpha W_t A' + (1-\alpha) W_0, A' = D^{-1/2} A D^{-1/2}$$

where D is the degree matrix and A' is the normalized adjacency matrix. The diffusion tuning parameter, $\alpha$ ($0<\alpha<1$), defines the distance that the prior knowledge weights can diffuse through the network. The optimal value of $\alpha=0.7$ reported for the STRING network was adopted. Adopting a convergence rule of $e=(W_{t+1}-W_t)<1e-6$, the above equation was solved iteratively for each drug to obtain the resulting smoothed weight vector $w_s$. The propagation results in lower-than-initial weights for the targets ($W<1$) and positive weights for all other genes within the network ($W>0$). The smoothed weight vector $w_s$ for each drug was then used to select the gene subset for the training pairs. The top-weighted 20 genes for all 208 drug compounds were pooled, and the resulting subset of the 2,128 most informative genes was used to profile each cell line in the dataset to select the bio data for the training pairs fed to the model.

The model architecture for this embodiment is illustrated schematically in FIG. 8. The model 55 comprises a gene attention encoder 56 which encodes the gene expression data of a training pair using attention weights $\alpha$. A SMILES attention encoder 57 encodes the SMILES string of the training pair using attention weights $\beta$. The encoded gene data from encoder 56 and the encoded SMILES data from encoder 57 were concatenated. The resulting encoded training pair is fed to a final set of dense feedforward layers 58, with weight-set $W_3$, to complete the regression. Network layers 58 comprises a 6-layered deep neural network with [512, 256, 128, 64, 32, 16] units in the layers and a sigmoidal activation designed by optimizing hyperparameters following a cross-validation scheme.

Gene attention encoder 56 comprises a softmax layer which produces the attention weights $\alpha_i$ for respective gene expression values $g_i$ in the training pairs, ensuring that the most informative genes receive a higher weight. The attention weights $\alpha_i$ are applied to the gene expression values $g_i$ in a dot product to produce the encoded gene data. The resulting gene attention weights $\alpha_i$ render the model more interpretable, identifying the genes that drive the sensitivity prediction in each cell line.

SMILES attention encoder 57 is based on an attention mechanism originally developed for document classification (see the Zichao Yang reference above) and here adapted to SMILES representations. The encoder 57 includes an initial tokenization stage 60 which tokenizes the input SMILES string as illustrated schematically in FIG. 9. An embedding layer of tokenization stage 60 transforms the raw SMILES strings into a sequence of vectors in an embedding space. The SMILES sequences were tokenized using a regular expression (here as described in the Schwaller reference above) to ensure charged or multi-character atoms (e.g., Cl or Br) were added as distinct tokens to the dictionary. The resulting atomic sequences of length T are represented as $E=\{e_1, \ldots, e_T\}$ with learned embedding vectors $e_i$ of length H for each dictionary token. The resulting tokenized strings (SMILES embeddings) of FIG. 9 correspond to block 61 of FIG. 8. The tokenized strings are then transformed into an attention space 62 of dimensions T×A. A learned vector V is combined with the atom annotations from the attention space through a dot product, the output of which is fed to a softmax layer which produces the vector of SMILES attention weights $\beta_i$. The input tokens were filtered with the attention weights, via a further dot product, to produce a single vector of hidden dimensionality H. The attention weights $\beta_i$ were computed as:

$$\beta_i = \frac{\exp(u_i)}{\sum_j^T u_j} \text{ where } u_i = V^T \tanh(W_e e_i + b)$$

The matrix $W_e \in \mathbb{R}^{A \times H}$ and the bias vector $b \in \mathbb{R}^{A \times 1}$ are learned in a dense layer.

The SMILES attention encoder 57 can be seen as a self-attention (SA) encoder which derives the attention weights based on the SMILES data alone. FIG. 10 illustrates another embodiment of a SMILES attention encoder for use in the FIG. 8 model. Elements corresponding to those of FIG. 8 are indicated by like reference numerals. This encoder 70 is a contextual-attention (CA) encoder that utilizes the gene expression subset G of the training pairs as context in determining the attention weights $\beta_i$ according to:

$$u_i = V^T \tanh(W_e e_i + W_g G)$$

where $W_g \in \mathbb{R}^{A \times |G|}$.

As illustrated in the figure, the matrices $W_g$ and $W_e$ first project both the gene expression data G and the embedded sequence element $e_i$ into the attention space A. The gene context vector 71 is then added to the projected token before combining with the learned vector V. Encoding the gene context vector with the projected token ultimately yields $\beta_i$ that takes into account the relevance of a compound substructure given a gene expression subset G.

The table of FIG. 11 indicates performance of the trained model structure of FIG. 8, with the SA encoder 57 and with the CA encoder 70 of FIG. 10, in comparison with a baseline model. The baseline model was based on the FIG. 8 architecture but excluded the SMILES encoder. The encoded SMILES data of FIG. 8 was replaced with Morgan fingerprints for the drug compounds. All models were trained with a 25-fold cross-validation scheme and returned normalized $IC_{50}$ values. The first results column of the table reports the best result for each set of 25 models in terms of RMSE (root mean square error) between predicted and true $IC_{50}$ values on test data. The second results column shows the average result across all 25 models. It can be seen that the models embodying the invention statistically significantly outperform the models trained on fingerprints.

Taking the best trained SA model (RMSE=0.089), its predictions for a selection of drugs and cell lines included in the test set were analysed. The results are indicated in the table of FIG. 12. This gives the predicted and true $IC_{50}$ values for 10 unseen drug-cell pairs within the test dataset. In addition, the top-5 attended genes given by gene attention weights are listed for each cell line. It can be seen that the model generated highly accurate predictions. Moreover, the genes highlighted by the computed attention weights showed a significant enrichment of the JAK-STAT signaling pathway, a known therapeutic target in cancer, demonstrating accurate interpretability.

It can be seen that, by using the raw string representation of drug compounds in combination with attention-based encoders, models generated by methods embodying the invention can significantly surpass the predictive performance of the baseline model using Morgan fingerprints. Moreover, the attention-based encoders of these models enable explanation and interpretation of observed results in the context of underlying biological and chemical processes.

It will be appreciated that numerous changes and modifications can be made to the exemplary embodiments described. For example, while exemplary implementations have been described for attention encoders 26 and 27 of FIG. 3, numerous other attention-based encoder architectures may be employed as will be apparent to those skilled in the art. Such encoders may include additional processing stages, such as initial recurrent or convolutional neural network layers, in some embodiments.

The subset of bio data included in training pairs may be selected in other ways, e.g. by simply selecting what is deemed (e.g. based on prior knowledge) to be an appropriate subset. Where feasible, all available bio data for cell samples might be used in some embodiments. Any other raw string representation, such as SMARTS strings, may be also be used in training pairs.

Methods embodying the invention may of course be applied to genetic diseases other than cancer. By way of example, other multifactorial genetic diseases displaying different subtypes caused by different genetic mutations include cardiovascular disease and Alzheimer disease.

In general, where features are described herein with reference to a method embodying the invention, corresponding features may be provided in a computer program product embodying the invention, and vice versa.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for treating a genetic disease, based on generating a neural network model for drug efficacy prediction in treatment of genetic disease from a dataset correlating biomolecular data for disease-cell samples with drug efficacy values for a plurality of drugs, the method comprising:
    defining training data pairs each comprising biomolecular data for a said sample and a string representation of a said drug;
    prior to defining said training data pairs:
        storing gene weights corresponding to respective genes in said samples, each gene weight being dependent on predetermined relevance of the respective gene to efficacy of a said drug;
        propagating said gene weights over a predetermined network indicating interaction between said genes to obtain smoothed gene weights for respective genes; and
        selecting a subset of genes in said samples in dependence on said smoothed gene weights for each drug;
        wherein said biomolecular data of a training data pair comprises biomolecular data for said subset of genes;
    using said training data pairs and said drug efficacy values corresponding to respective pairs to train weights of a neural network model comprising a first attention-based encoder which encodes said biomolecular data of each pair, using a first set of said weights, to produce encoded biomolecular data, a second attention-based encoder which encodes said string representation of each pair, using a second set of said weights, to produce encoded string data, and a set of neural network layers which process the encoded biomolecular and string data for each pair, using a third set of said weights, to produce a model output corresponding to drug efficacy;
    storing the trained model for drug efficacy prediction;
    repeatedly selecting a drug, defining an inference data pair comprising biomolecular data for a disease-cell sample and a string representation of a drug to be tested for efficacy in relation to that sample, and obtaining a prediction of drug efficacy by supplying the inference data pair to the trained model; and
    treating the genetic disease with the drug that has the greatest predicted efficacy.

2. The method as claimed in claim 1 wherein:
    each gene weight comprises one of a higher value and a lower value dependent on predetermined relevance and non-relevance respectively of the corresponding gene to efficacy of the drug; and said subset is selected by selecting, for each drug, a plurality of genes having the highest smoothed gene weights for that drug.

3. The method as claimed in claim 1 wherein said biomolecular data comprises gene expression data.

4. The method as claimed in claim 1 wherein the second attention-based encoder tokenizes said string representation and encodes the tokenized string representation using the second set of weights.

5. The method as claimed in claim 1 wherein the second attention-based encoder comprises a contextual-attention encoder which encodes said string representation of each pair with a context vector comprising said biomolecular data of that pair.

6. The method as claimed in claim 1 further comprising, after storing the trained model:
defining an inference data pair comprising biomolecular data for a disease-cell sample and a string representation of a drug to be tested for efficacy in relation to that sample; and
supplying the inference data pair to the trained model to obtain a model output predictive of efficacy of the drug.

7. The method as claimed in claim 6 including:
defining a plurality of inference data pairs comprising biomolecular data for respective disease-cell samples for a disease and said string representation of the drug; and
supplying the inference data pairs to the trained model to obtain a plurality of model outputs collectively predictive of efficacy of the drug in treatment of that disease.

8. The method as claimed in claim 1 further comprising, after storing the trained model:
receiving biomolecular data for a disease cell-sample of a patient;
defining an inference data pair comprising said biomolecular data of the patient and a string representation of a drug to be tested for efficacy in treatment of that patient;
supplying the inference data pair to the trained model to obtain a model output predictive of efficacy of the drug; and
outputting the model output for use in treatment planning for the patient.

9. The method as claimed in claim 1 wherein said disease-cell samples comprise cancer-cell samples.

10. The method as claimed in claim 1, further comprising:
defining a plurality of inference data pairs comprising biomolecular data for a respective disease-cell samples for a disease and said string representation of the drug; and
supplying the inference data pairs to the neural network model to obtain a plurality of model outputs collectively predictive of efficacy of the drug in treatment of that disease.

11. The method as claimed in claim 1, further comprising:
receiving biomolecular data for a disease cell-sample of a patient, wherein said inference data pair comprises said biomolecular data of the patient such that said model output is predictive of efficacy of the drug in treatment of that patient; and
outputting the model output for use in treatment planning for the patient.

* * * * *